US012767916B2

(12) United States Patent
Heeren

(10) Patent No.: US 12,767,916 B2
(45) Date of Patent: Oct. 20, 2026

(54) SAMPLING APPARATUS FOR CELL CULTURE BED AND RELATED METHODS

(71) Applicant: UNIVERCELLS TECHNOLOGIES S.A., Nivelles (BE)

(72) Inventor: Bart Karel Johan Heeren, Brussels (BE)

(73) Assignee: UNIVERCELLS TECHNOLOGIES S.A., Nivelles (BE)

(*) Notice: Subject to any disclaimer, the term of this patent is extended or adjusted under 35 U.S.C. 154(b) by 914 days.

(21) Appl. No.: 17/981,568

(22) Filed: Nov. 7, 2022

(65) Prior Publication Data

US 2023/0146372 A1 May 11, 2023

Related U.S. Application Data

(60) Provisional application No. 63/276,621, filed on Nov. 7, 2021.

(51) Int. Cl.
*C12M 1/26* (2006.01)
*C12M 1/00* (2006.01)
*C12M 1/12* (2006.01)

(52) U.S. Cl.
CPC ............ *C12M 33/04* (2013.01); *C12M 23/32* (2013.01); *C12M 25/04* (2013.01)

(58) Field of Classification Search
CPC ...... C12M 33/04; C12M 23/32; C12M 25/04; C12M 23/26; C12M 33/00; C12M 25/18
See application file for complete search history.

(56) References Cited

U.S. PATENT DOCUMENTS

| | | | | |
|---|---|---|---|---|
| 5,266,476 A * | 11/1993 | Sussman | C12M 23/20 435/399 |
| 2010/0099127 A1* | 4/2010 | Bodner | C12M 23/08 435/309.1 |
| 2013/0071872 A1* | 3/2013 | Ho | C12M 33/04 422/547 |
| 2014/0030805 A1* | 1/2014 | Kasuto | C12M 47/02 435/366 |

(Continued)

FOREIGN PATENT DOCUMENTS

| | | | |
|---|---|---|---|
| WO | WO-2019175442 A1 * | 9/2019 | C12M 33/02 |
| WO | WO2022216568 A1 | 10/2022 | |

*Primary Examiner* — William H. Beisner
*Assistant Examiner* — Danielle B Henkel
(74) *Attorney, Agent, or Firm* — Dickinson Wright PLLC; Andrew D. Dorisio; Nicholas P. Coleman

(57) ABSTRACT

An apparatus for sampling a cell culture includes a sampler for connecting to a bioreactor with a fixed bed including the cell culture. A releasably attached sample portion for positioning within or adjacent the fixed bed includes a substrate on which cells may be grown and then removed from the bioreactor to provide an indication of cell growth. A kit for sampling a cell culture bed of a bioreactor includes the sampler for sampling the cell culture bed with the releasably attached sample portion, along with a container adapted to detach the sample portion from the sampler. A method of obtaining a sample of a cell culture in a bed within a bioreactor includes positioning a sampler positioned at least partially in or adjacent to the bed to promote the growth of cells on a releasably attached portion of the sampler, withdrawing the sampler from the bioreactor, and detaching the portion of the sampler.

15 Claims, 23 Drawing Sheets

(56) References Cited

U.S. PATENT DOCUMENTS

| | | | | |
|---|---|---|---|---|
| 2016/0281045 | A1* | 9/2016 | Mccall | C12M 23/40 |
| 2019/0031998 | A1* | 1/2019 | Valonen | C12M 1/02 |
| 2020/0165557 | A1* | 5/2020 | Lesch | C12M 29/18 |
| 2024/0368516 | A1* | 11/2024 | Blakeley | C12M 25/02 |

* cited by examiner

SAMPLING APPARATUS FOR CELL CULTURE BED AND RELATED METHODS

This patent application claims the benefit of U.S. Provisional Patent Application. Ser. No. 63/276,621, filed Nov. 7, 2021, the disclosure of which is incorporated herein by reference. This application is related to International Patent Application WO 2019/175442, U.S. Provisional Patent Application Ser. Nos. 62/728,405, 62/644,014, Belgian Patent Application BE2018/5179, U.S. Patent Application Publication No. 2018/0282678, International Patent Application PCT/EP2018/076354, U.S. Provisional Patent Application 62/711,070, and U.S. Provisional Patent Application 62/725,545, the disclosures of which are incorporated herein by reference.

TECHNICAL FIELD

This document relates generally to the cell culturing arts and, more particularly, to a sampling device for a cell culture bed, such as for example, one in a bioreactor including a fixed bed.

BACKGROUND

Certain cell culturing devices, such as bioreactors, use a "fixed bed" for the growth of cells that are entrapped thereon or for the growth of adherent cells which attach and grow thereon. These high cell density bioreactors suffer from the inherent inability of its users to easily take samples during the culture process for various purposes (e.g., to take cell-associated measurements such as those relating to viability and density). Past approaches for in-process sampling from a fixed bed involve reaching inside the bioreactor with an extraction tool, such as tweezers, to manually extract a piece or portion of the bed or a sample thereof. This operation is difficult as it requires careful dexterity, and invariably causes undesirable perturbations that risk disrupting the cell culture environment, as well as the sample specimen. Sterility must also be maintained during the entire bioprocessing operation, which requires the operator collecting the sample to follow precise aseptic operating procedures, and may be particularly challenging when simultaneously introducing an extraction tool.

Furthermore, to maintain the necessary sterile conditions, the bioreactor is typically located inside a containment unit, such as a laminar flow cabinet or a biosafety cabinet. This limits an operator's access, as well as their freedom of movement. While a small scale bioreactor may be fully placed in such a containment unit, a large, production-scale version cannot readily be placed in such a cabinet to achieve this result.

Sterile (or aseptic) sensors, such as so-called "biomass" sensors have been proposed for assessing cell density. However, many known sensors lack sufficiently robust technology, and do not allow for the actual direct examination of the cells as a sample. Indirect measurement of cell characteristics by the biomass sensor may also be far less accurate than direct examination of cells.

Moreover, as opposed to the case of fluidized beds or classical agitated bioreactors where sampling of the liquid in which the cells reside is possible, a sterile liquid sensor in a fixed bed bioreactor yields only information from which an educated guess or estimate can be made regarding cell conditions based on detected byproducts (metabolites) of the growth process left in the fluid. Thus, current samplers and methods do not provide an accurate and timely tool for developing a reliable cell culture process for a fixed bed bioreactor.

Accordingly, a need is identified for an apparatus that provides the ability to take a reliable sample from the cell culture bed and the cells associated therewith. The apparatus would allow for the sample to be obtained in an easy and inexpensive manner, would protect against contamination (both internal to the bioreactor and external to it), and/or also avoid creating deleterious disruptions of the cell culture environment.

SUMMARY

An object of the invention is to provide a device that enables the taking of one or more samples from the cell culture in an easy, inexpensive, and reliable manner, without risking contamination, and also while avoiding creating deleterious disruptions of the cell culture environment.

According to a first aspect of the disclosure, a bioreactor with integrated cell sampling capability is provided. The bioreactor includes a housing including a sampling port. A fixed bed is positioned within the housing. A cell sampler extending through the sampling port and including a releasably attached sample portion positioned within or adjacent to the fixed bed.

In one embodiment, the releasably attached sample portion includes a substrate adapted for growing cells thereon during cell culture. The sampler includes a positioner adapted for positioning the releasably attached sample portion within or adjacent to the fixed bed. The releasably attached sample portion is connected to the positioner by a frangible connection. The positioner may be associated with the sampling port.

In these or other embodiments, the bioreactor includes a cap for sealing the sampling port. The sampler may be releasable from a grip located external to the bioreactor. The sampler may be adapted for selectively forming a locking engagement with the bioreactor housing. The bioreactor housing includes a lid and the lid comprises the sampling port.

The fixed bed may comprise a plurality of layers. The releasably attached sample portion of the sampler may be positioned between the plurality of layers.

According to a further aspect of the disclosure, an apparatus for sampling a cell culture associated with a fixed bed in a bioreactor having a port is provided. The apparatus comprises a sampler including a releasably attached sample portion adapted for positioning in the bioreactor adjacent the fixed bed. The sample portion includes a substrate adapted for growing cells.

In one embodiment, the releasably attached sample portion includes a frame for receiving the substrate. The sampler includes a grip connected to a positioner for positioning the releasably attached sample portion in the bioreactor. The sampler may be adapted for selectively forming a locking engagement with the bioreactor. The sample portion may be releasably attached to the sampler by a frangible connection.

Still a further aspect of the disclosure relates to a kit for sampling a fixed bed of a bioreactor. The kit comprises a sampler for sampling the fixed bed, the sampler including a releasably attached sample portion. The kit further comprises a container adapted to detach the releasably attached sample portion from the sampler.

In one embodiment, the container includes an insert for receiving the releasably attached sample portion, the insert adapted to facilitate detaching the releasable sample portion from the sampler. The releasably attached sample portion may include a substrate for growing cells.

Yet another aspect of the disclosure relates to a method of obtaining a sample of a cell culture in a fixed bed bioreactor including a sampler at least partially positioned in or adjacent to the fixed bed to promote the growth of cells on a releasably attached portion of the sampler. The method comprises initiating the cell culture process in the bioreactor, and allowing the process to run for a period of time to permit cell growth in the fixed bed and the releasably attached portion. The method further comprises withdrawing the sampler from the bioreactor, and detaching the releasably attached portion from the sampler. In one embodiment, the detaching step comprises inserting the releasably attached portion into an opening of an insert in a container, and using the insert to break the portion from the sampler.

BRIEF DESCRIPTION OF THE DRAWING FIGURES

The novel features of the disclosure are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

Figure 2:
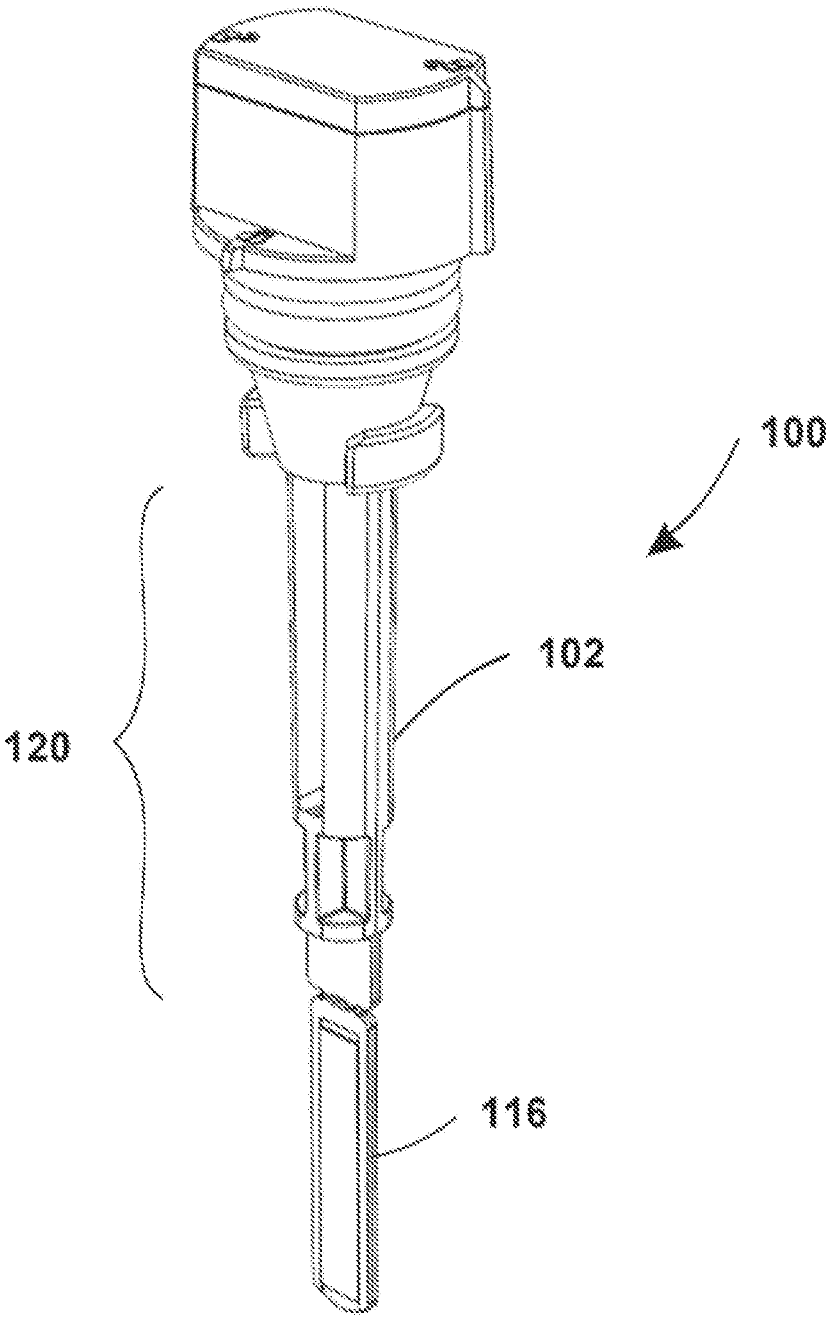
Figure 3:
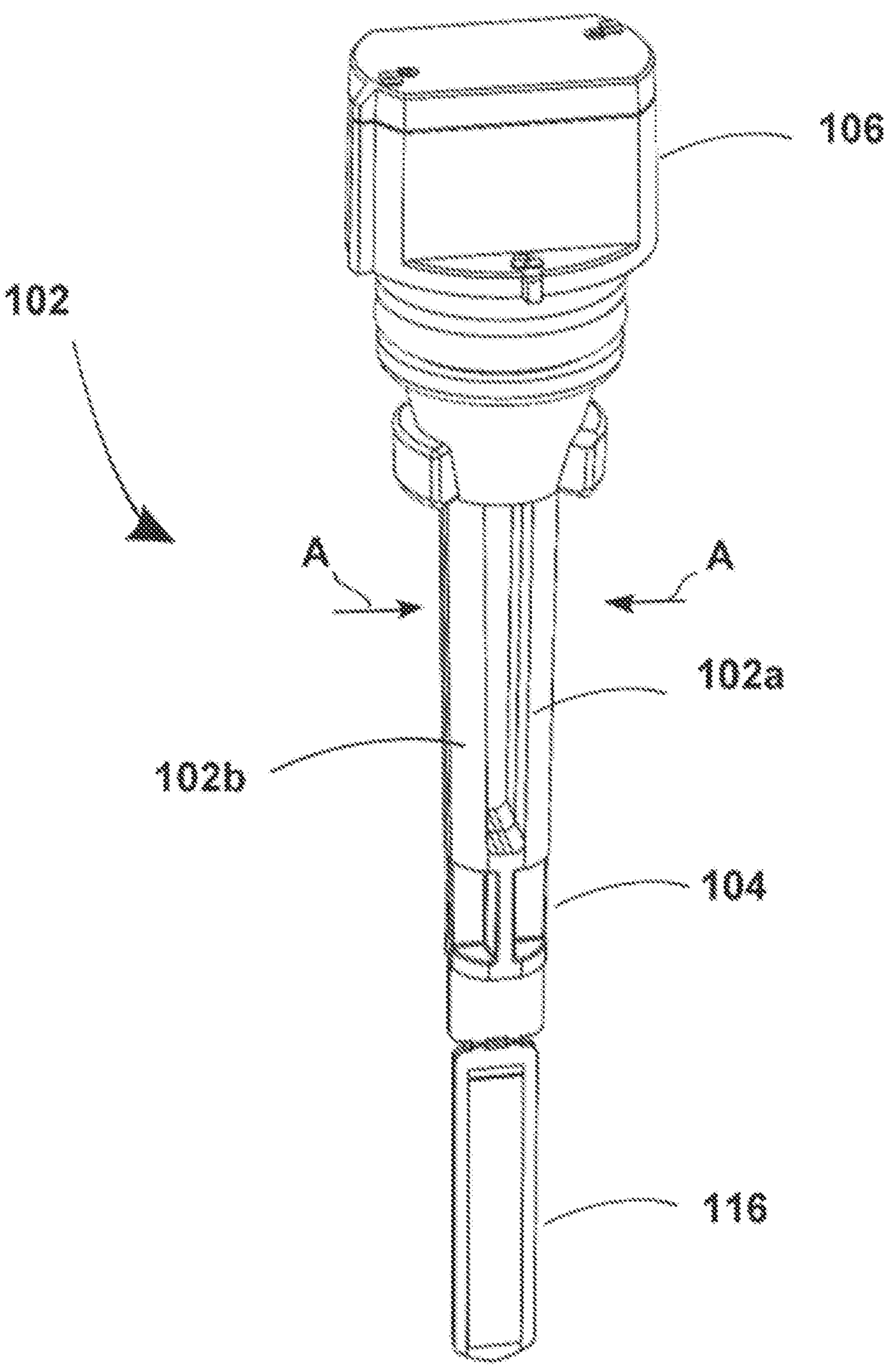
Figure 4:
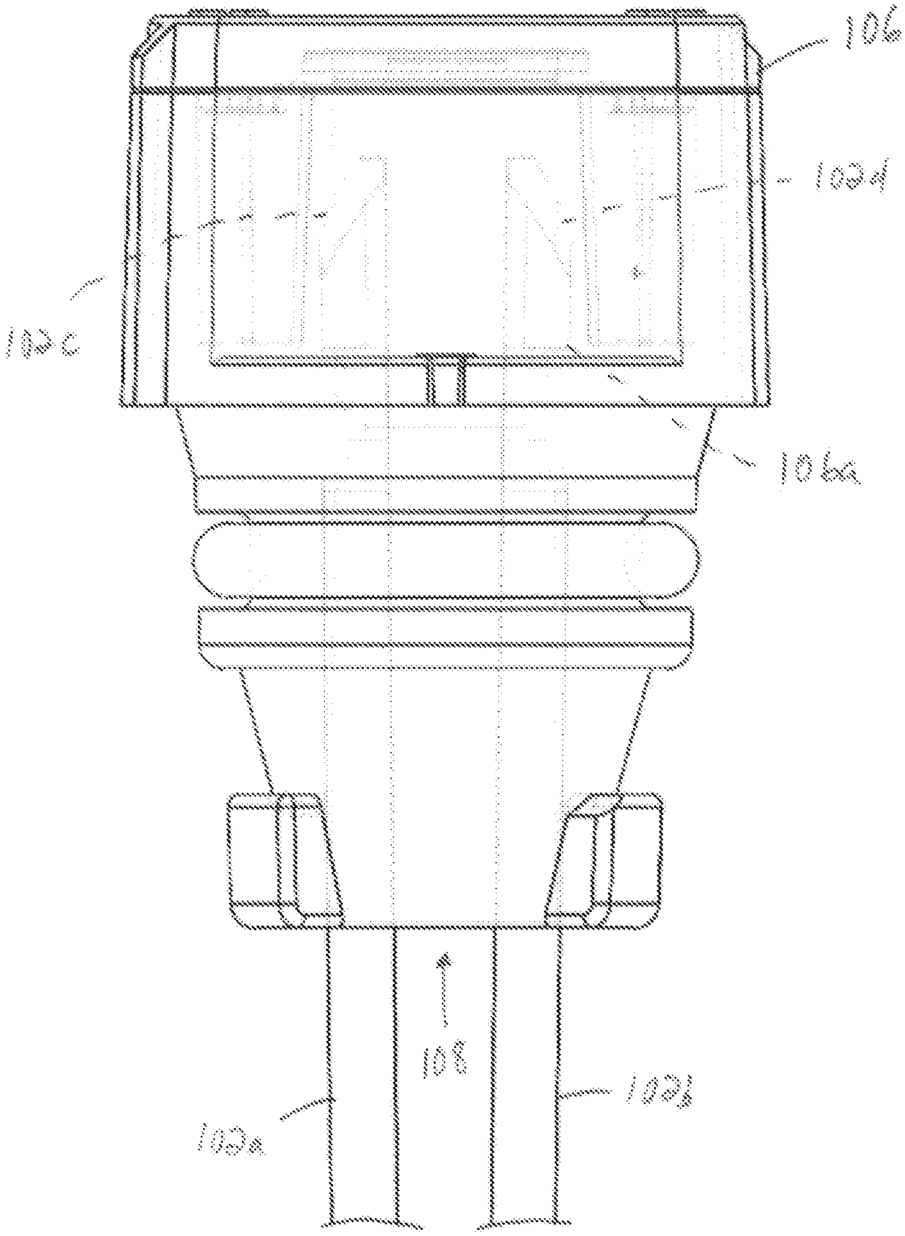

FIGS. 2, 3, and 4 illustrate a sampler according to one aspect of the disclosure.

FIGS. 5, 5A, 5B and 6 illustrate a positioner forming part of the sampler of FIGS. 2, 3, and 4.

Figure 7:
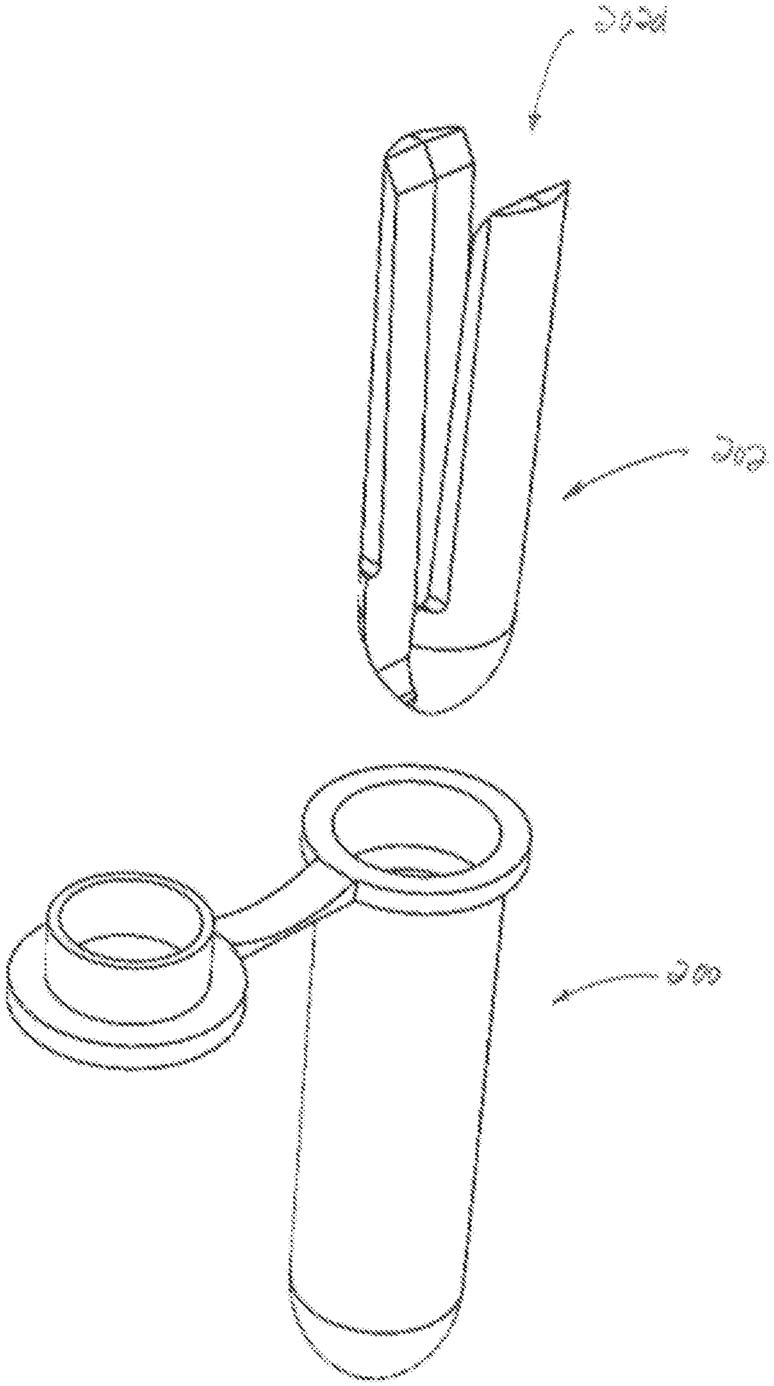
Figure 8:
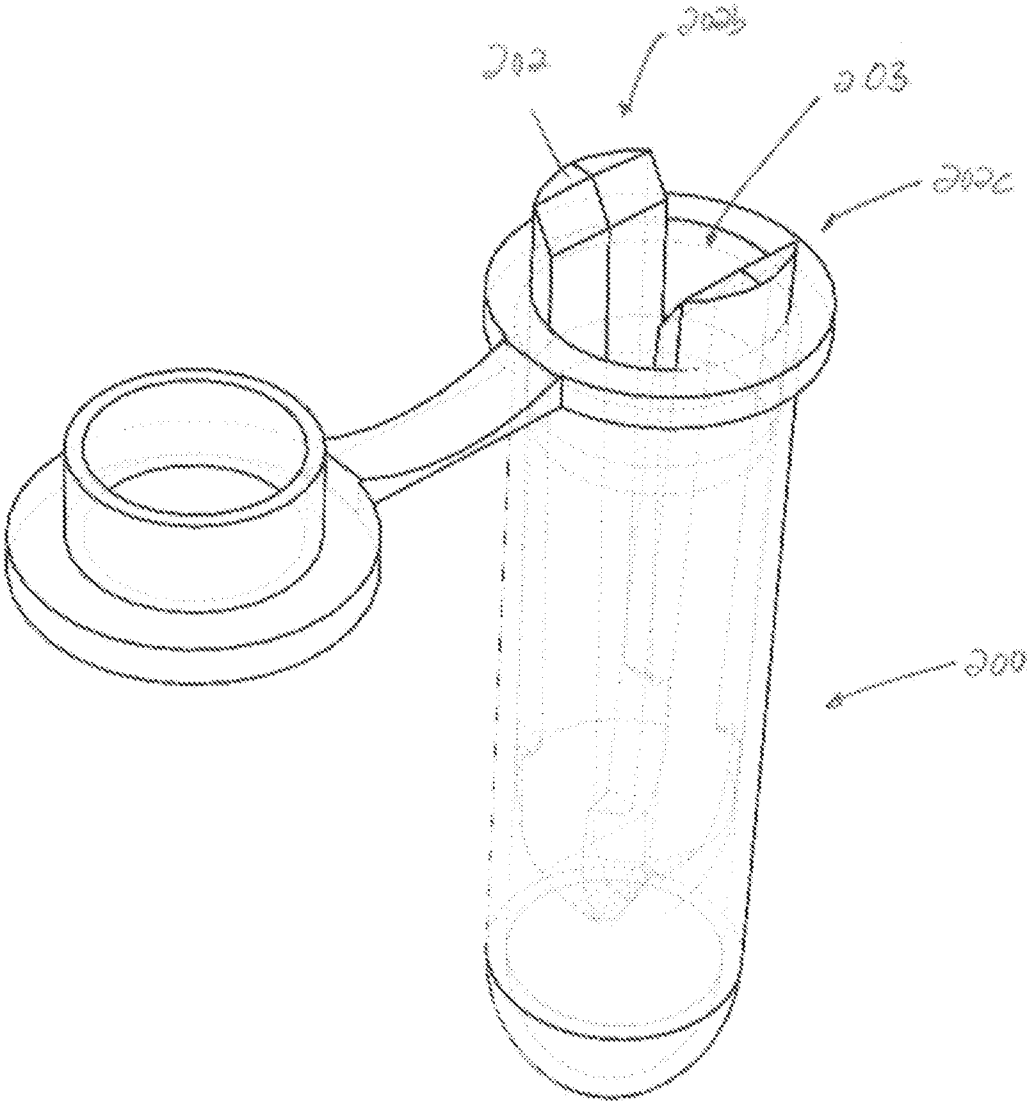

FIGS. 7 and 8 illustrate an embodiment of a container including an insert for receiving a sample portion of the sampler.

Figure 9:
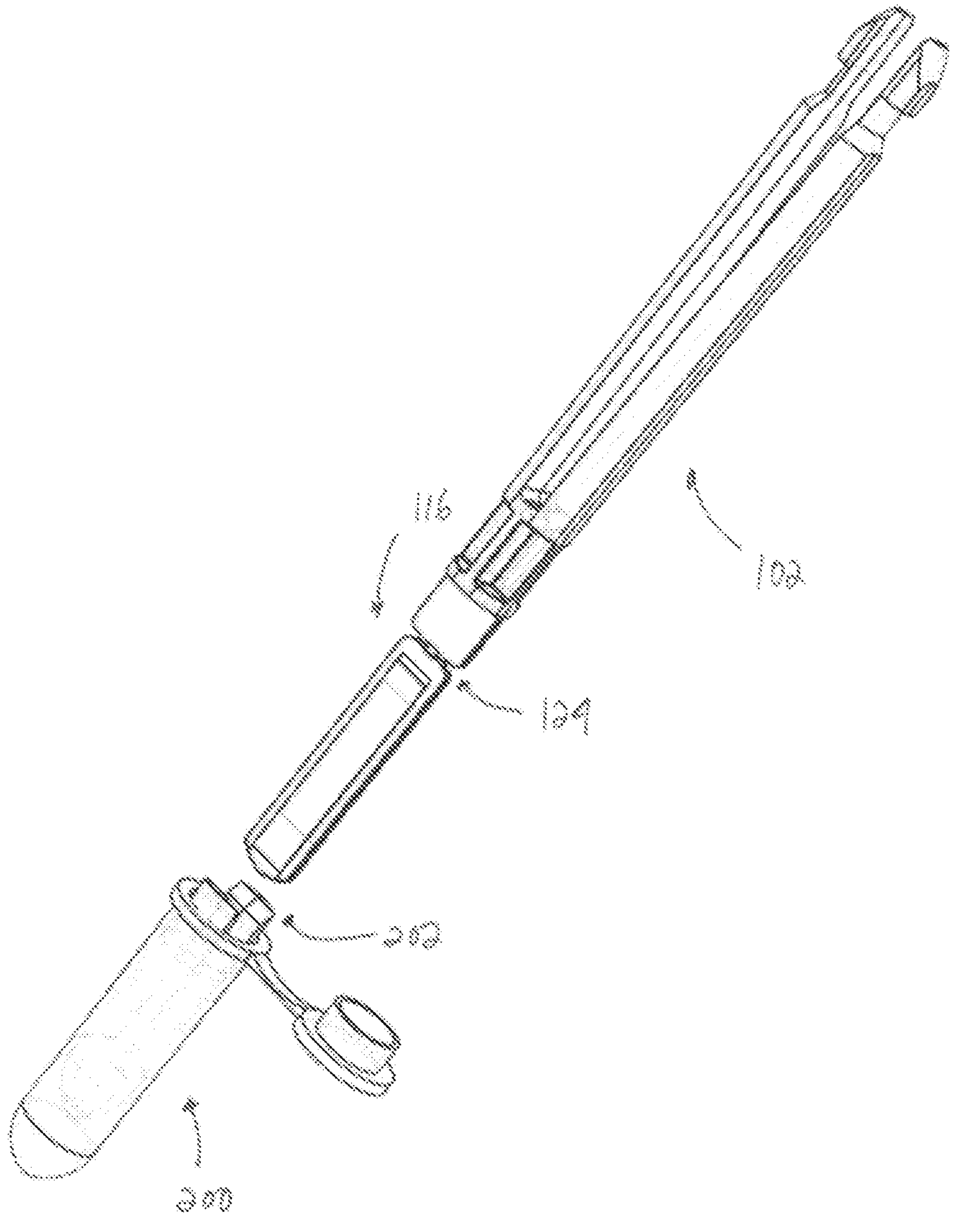
Figure 9A:
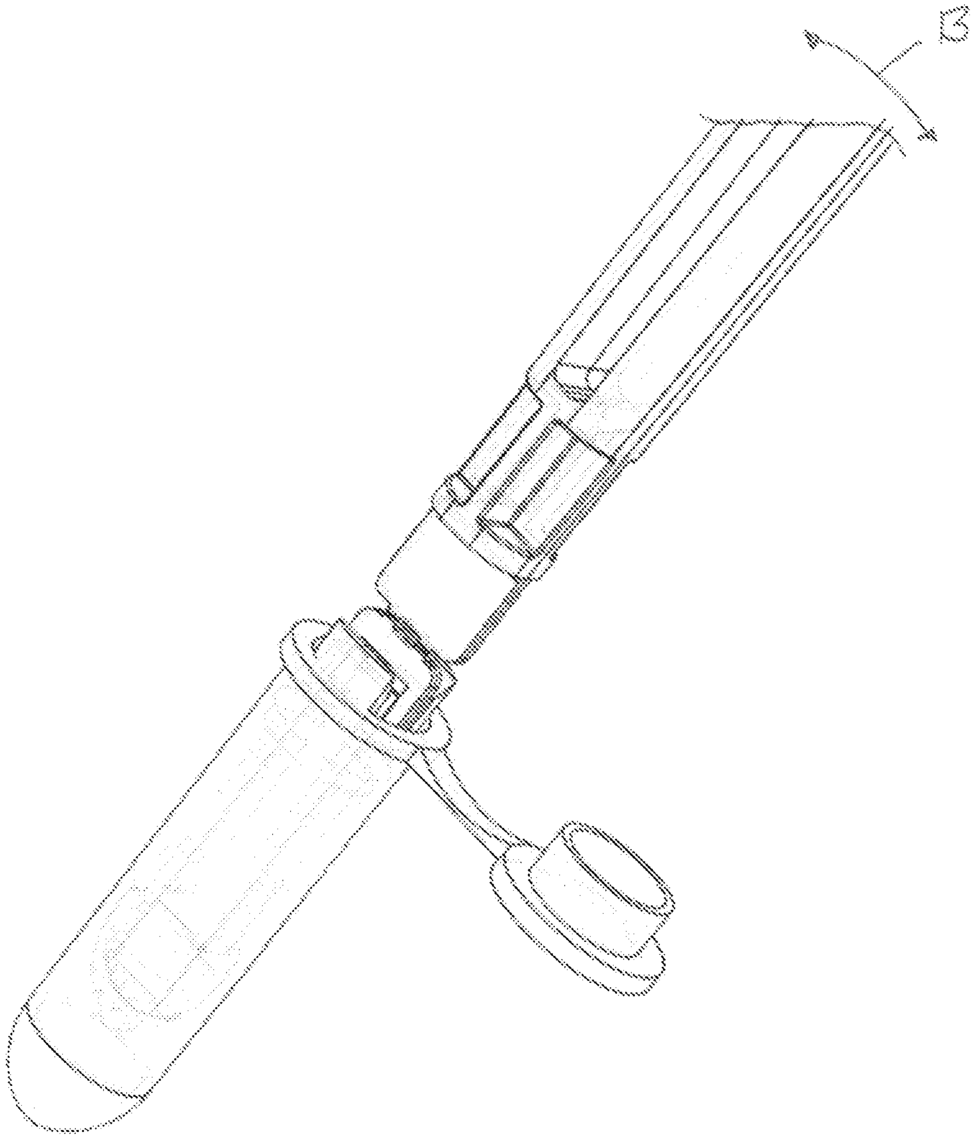
Figure 10:
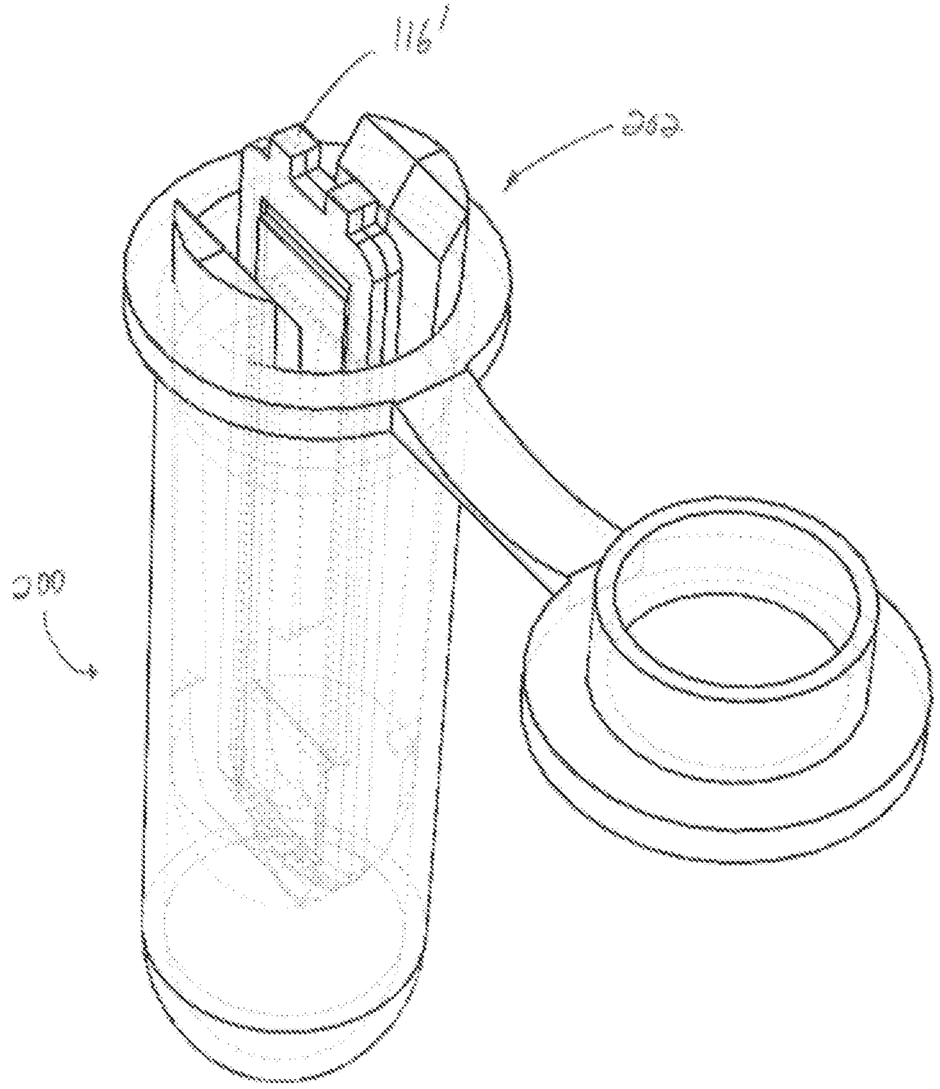

FIGS. 9, 9A and 10 illustrate the manner in which the sample portion may be detached from the sampler when associated with the container and insert.

Figure 11:
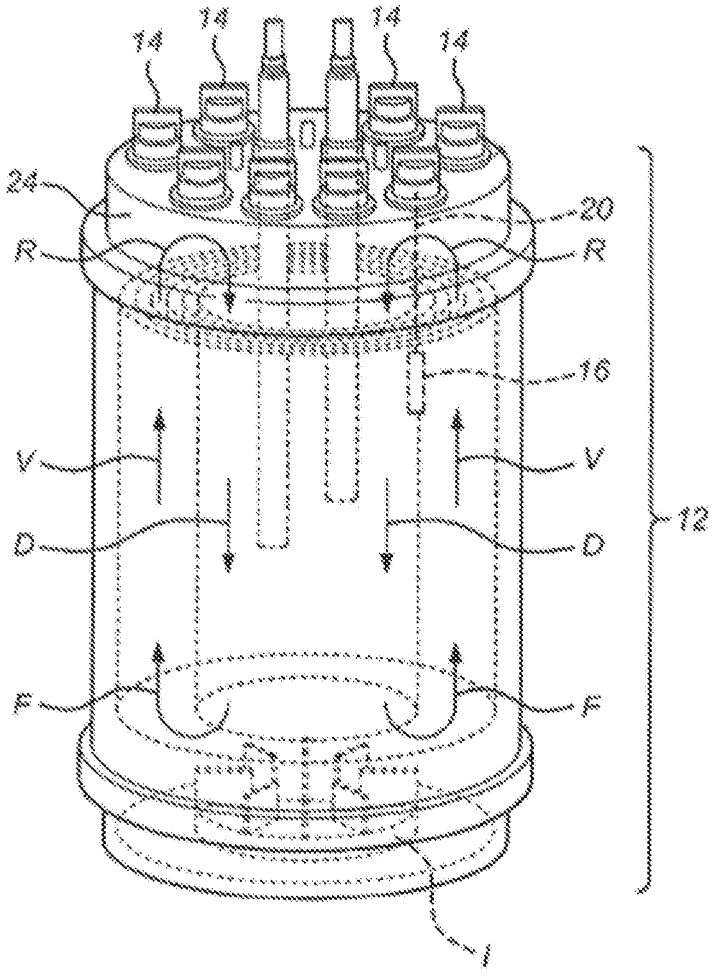

FIG. 11 is one example of a fixed bed bioreactor for possible application of the sampler.

Figure 12:
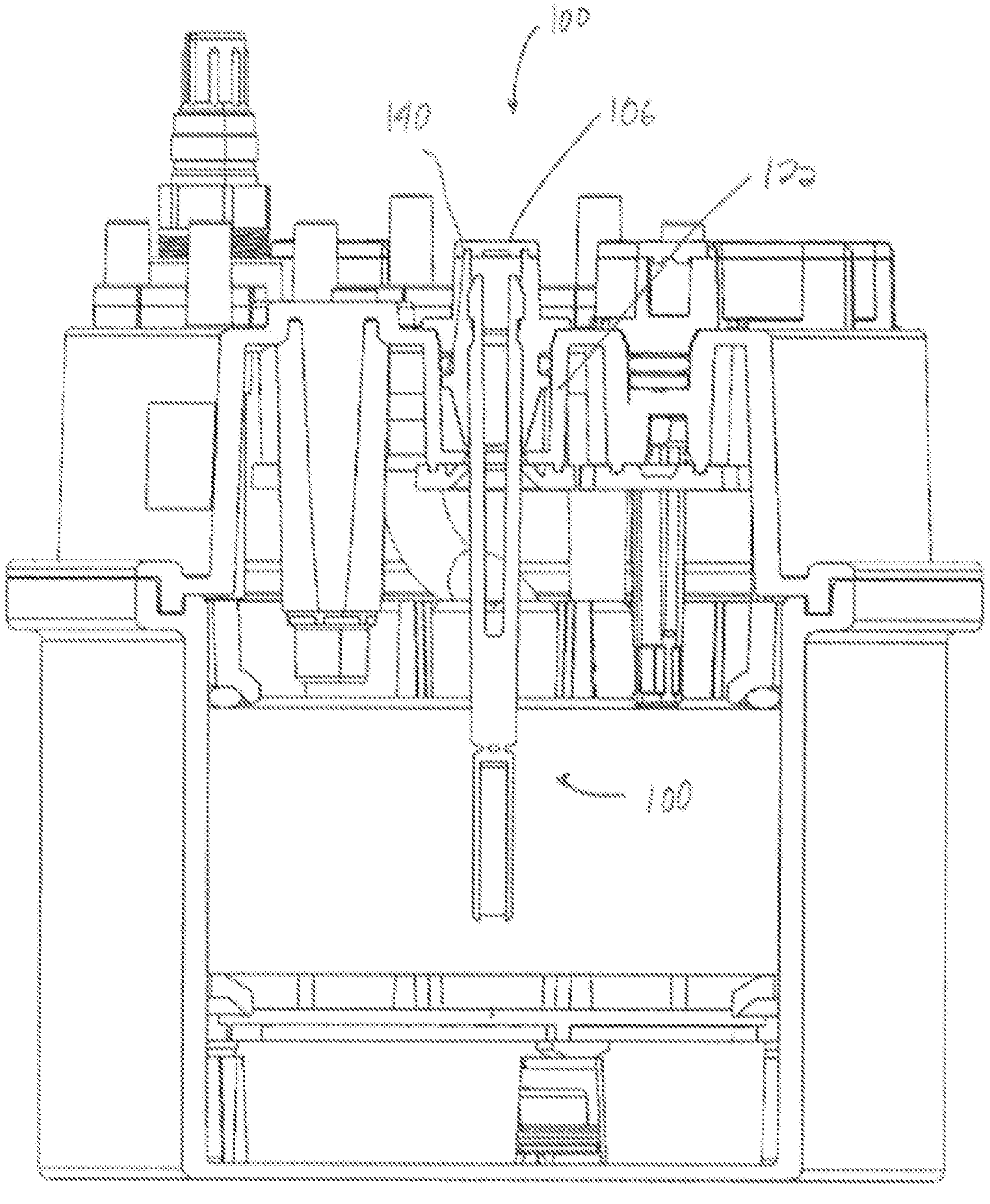
Figure 12A:
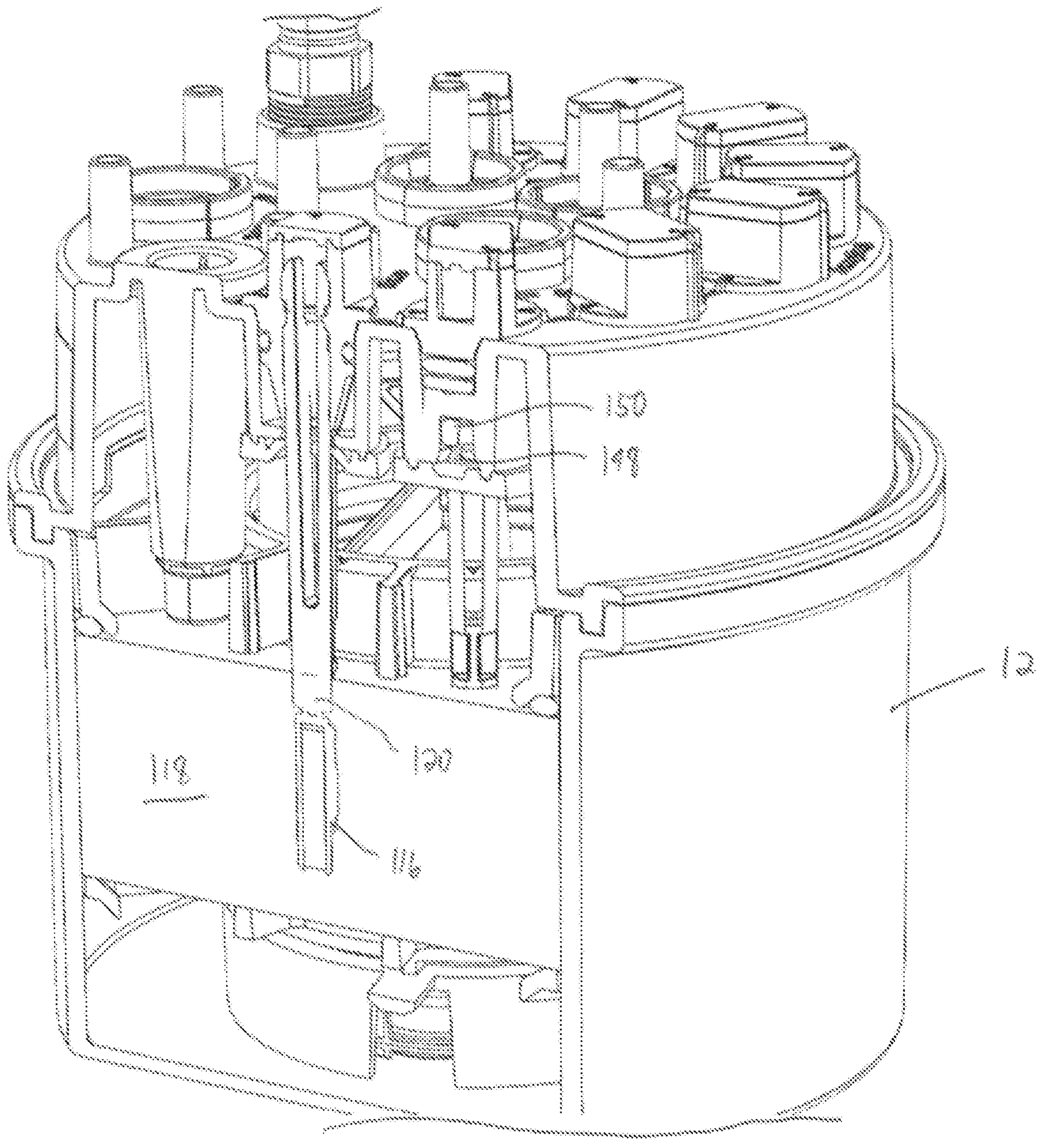
Figure 12B:
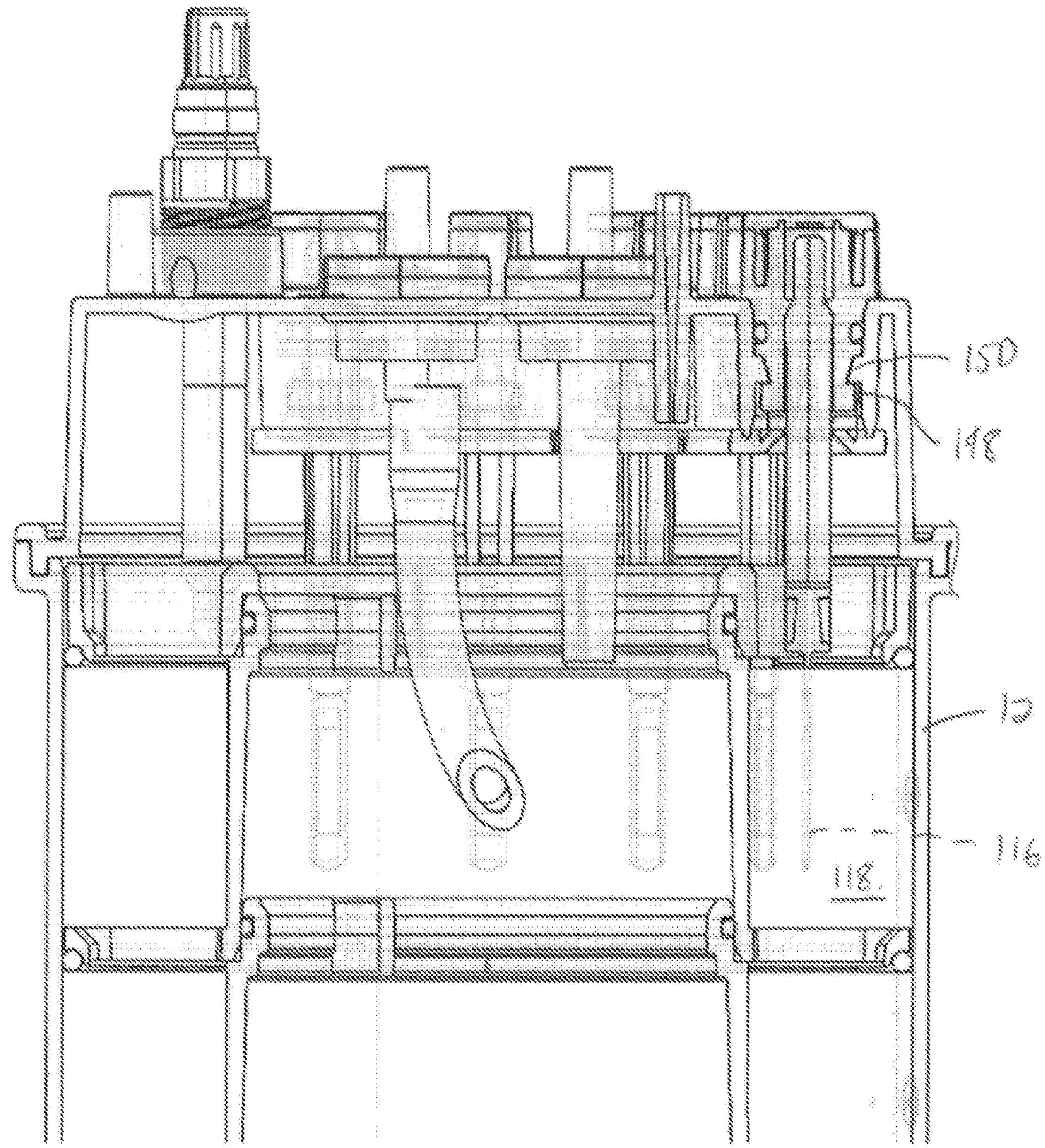

FIGS. 12, 12A, and 12B are partially cutaway, cross-sectional views of the bioreactor of FIG. 11.

Figure 13:
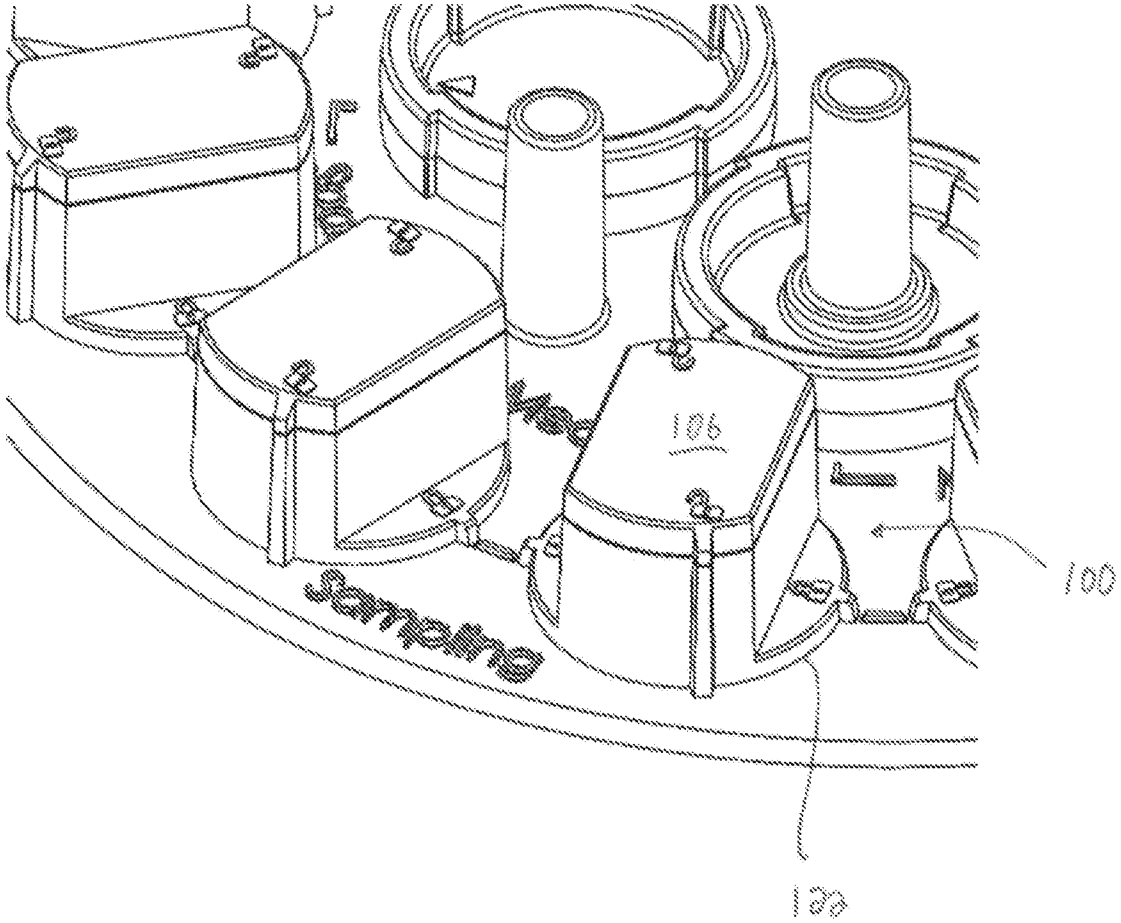
Figure 14:
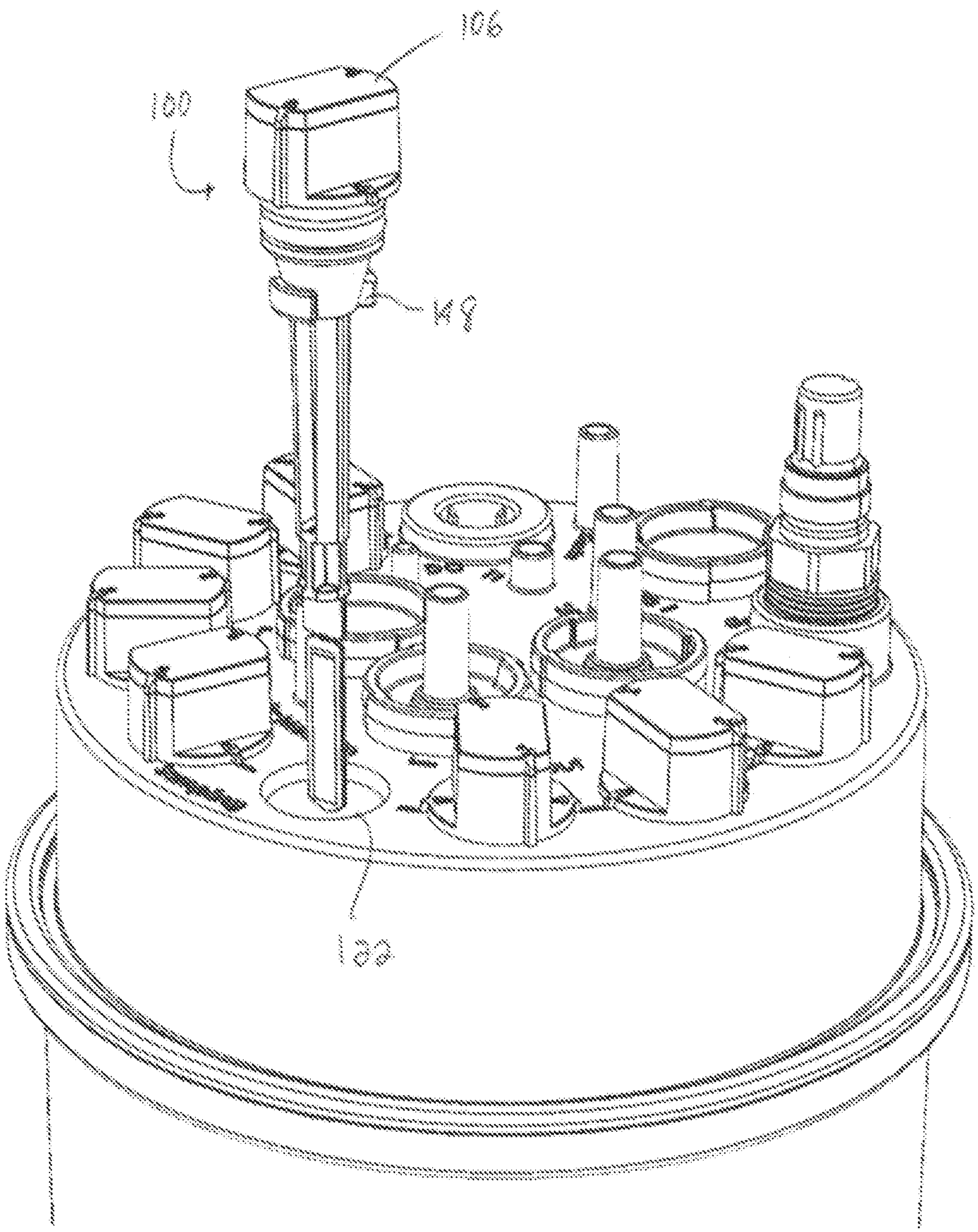

FIGS. 13 and 14 illustrate a locked and unlocked condition of the sampler when associated with a bioreactor.

Figure 15:
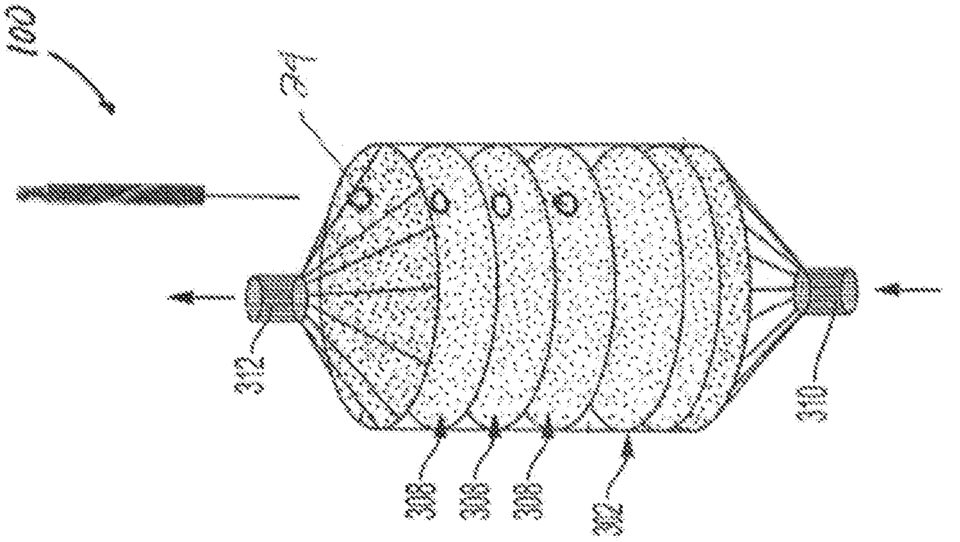
Figure 16:
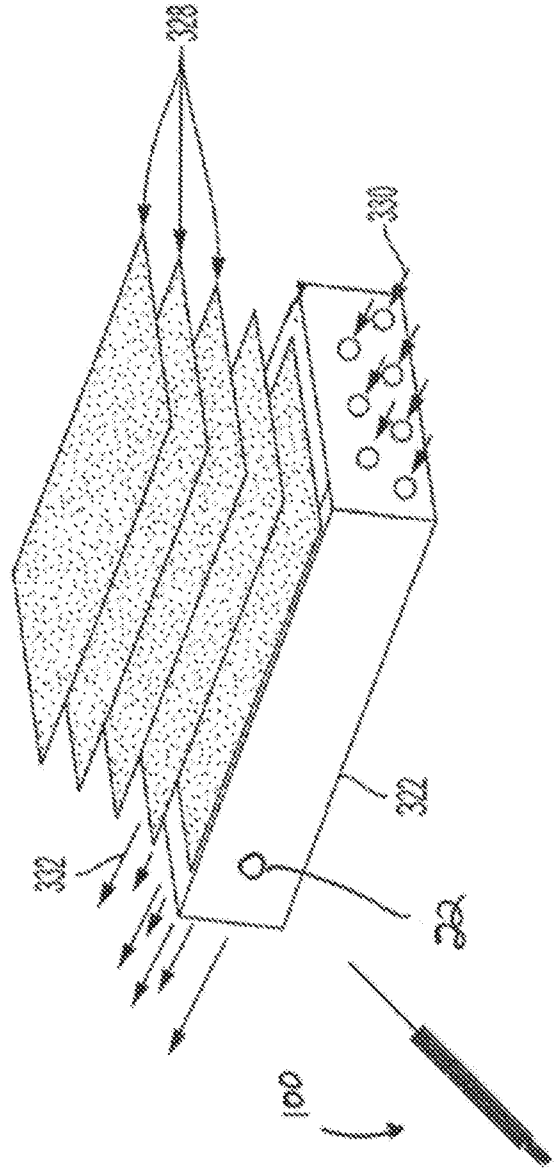

FIGS. 15 and 16 show alternate versions of bioreactors.

DETAILED DESCRIPTION

Figure 1:
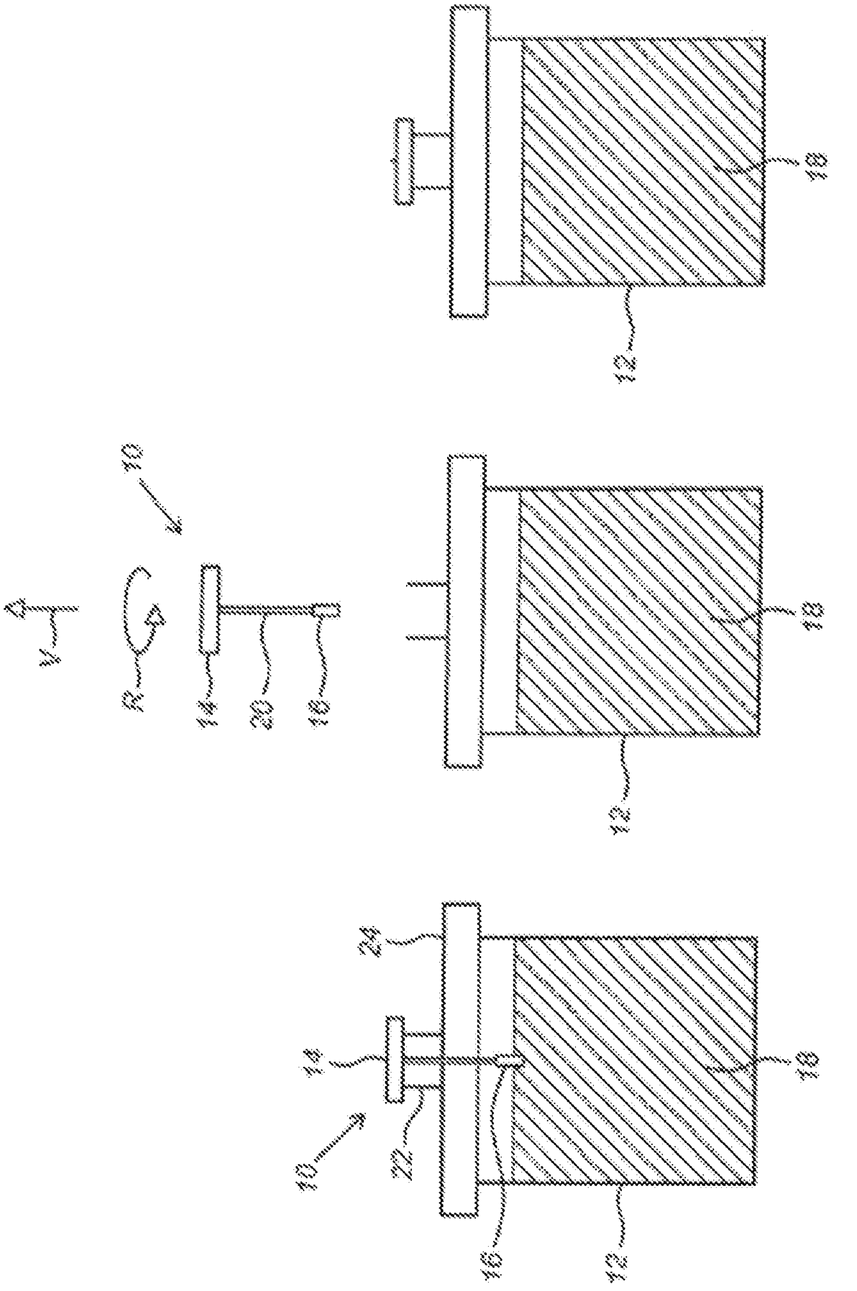
FIG. 1 is a schematic view of a first embodiment of a sampler for a cell culture system, such as a bioreactor, according to the disclosure.

Reference is now made to FIG. 1, which illustrates a sampler 10 for a cell culturing apparatus, such as for example a bioreactor 12, fermenter or the like, according to one aspect of the disclosure. For purposes of this example, the bioreactor 12 may be presumed to operate under external sterile conditions, such as in a containment unit (e.g., a laminar flow cabinet, external isolator or the like). However, as outlined further in the description that follows, the sampler 10 may also be used in other environments.

The sampler 10 may comprise a support portion for associating with an opening or port in the bioreactor 12 providing access to an interior compartment thereof. In the illustrated embodiment, the support portion takes the form of a cover or cap 14 for sealing the port in the bioreactor 12, thus maintaining the sterility of the interior compartment, even when the bioreactor 12 is not in a containment unit. The support portion, or cover/cap 14 in this version, may support a sample portion 16 for positioning within a fixed bed 18 in the interior compartment of the bioreactor 12. The sample portion 16 may be removable from both the fixed bed 18 and the support portion, as outlined further in the following description.

The sample portion 16 may comprise a substrate (such as, for example, a sheet of material, a sheet of flexible material, or the like, which sheet may be in the form of an elongated strip) which, like the fixed bed itself, is adapted to promote cell growth or cell immobilization/entrapment. The substrate may alternatively comprise one or more fibers, including those arranged as a piece of nonwoven material, as outlined further in the following description. The sample portion 16 may be a separate structure for positioning within the fixed bed 18 during the process of assembling the bioreactor 12 (as outlined further in the following discussion). In such case, the sample portion 16 may be adapted for detachment and removal from the remainder of the fixed bed 18.

The sample portion 16 may be removably attached to a positioner 20. The positioner 20 facilitates holding the sample portion 16 in an appropriate position in or adjacent to the fixed bed 18, and also facilitates removing it from the fixed bed 18. Prepositioning of the sample portion 16 within the fixed bed 18 may be achieved by hand via the positioner 20, or by using a tool, such as tweezers (not shown), to pass the sample portion 16 into or adjacent the fixed bed 18 through a port 22 in the lid 24 of the bioreactor 12 (but could be achieved by removing the lid entirely). This placement may be done prior to the commencement of the bioprocessing operation, including possibly during assembly of the bioreactor (including after the sample portion 16 if separate is placed in the fixed bed) or as a part of the process of manufacturing and assembling the fixed bed 18.

The fixed bed 18 may comprise any substrate for achieving cell growth or cell immobilization, and may comprise, for example, a structured fixed bed (which means that it is formed of an easily replicated, generally homogeneous, substantially fixed structure, and thus is not randomly oriented or unstructured, yet, as can be appreciated, could take a variety of sizes or shapes while meeting this qualification). The material of the fixed bed 18 may be woven, non-woven, a fiber matrix, or other forms, and may be formed of various polymer materials, including but not limited to polyethylene and polyethylene terephthalate. In one embodiment, as shown in a top view in FIG. 1A, the fixed bed 18 comprises a non-woven material 18*a* arranged in at least two layers on and within which cells grow, thereby forming a structured fixed bed. These layers are thus considered cell immobilization layers.

In the particular form shown, the non-woven material 18*a* is arranged in a rolled or spiral fashion, with each of the two cell immobilization layers separated by spacer layers 18*b*, which promote culture and media flow between the various layers. The sample portion 16 may be a separate substrate positioned (as shown) between two of the layers of the bed 18 in rolled or spiral form, such as cell immobilization (or non-woven material) layers 18*a*. Alternatively, the sample portion 16 may be located between a spacer layer and an adjacent cell immobilization layer. The fixed bed 18 may have only a single cell immobilization layer alternatively in roll or spiral with a single spacer layer.

However, the above is merely one example, and is not intended to limit the manner in which the sample portion 16 may be associated with a fixed bed 18 of any known form (e.g., positioning within a fiber matrix, or an arrangement of layers that are not spirally wound). For instance, FIG. 1B illustrates a non-structured fixed bed, which may comprise a plurality of randomly oriented fibers 18*c*. In this embodiment, the sample portion 16 may comprise one of the fibers 18*c*. This fiber 18*c* may be connected to the positioner 20, as indicated (or as a substrate of non-woven fibers). Alternatively, more than one fiber can be connected to the positioner 20 and act as the sample portion (such as a woven or non-woven material, as noted previously).

Figure 1A:
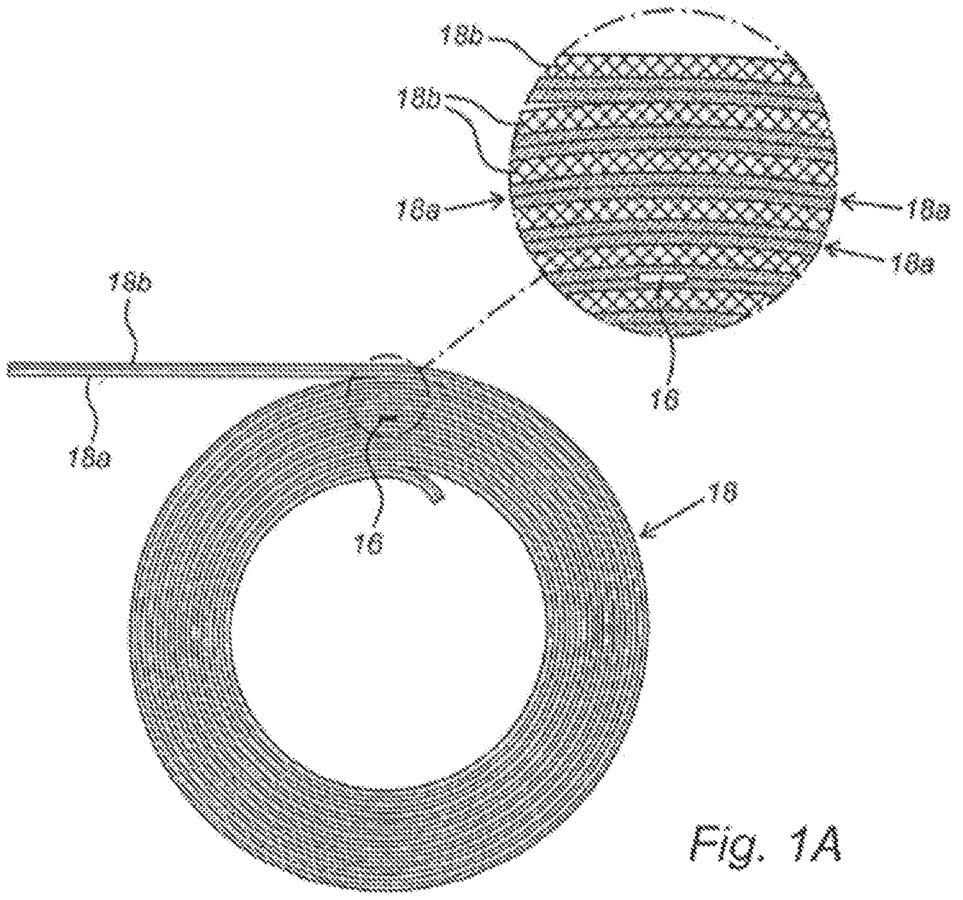
FIG. 1A illustrates one example of a structured fixed bed in the form of a spiral bed.
Figure 1B:
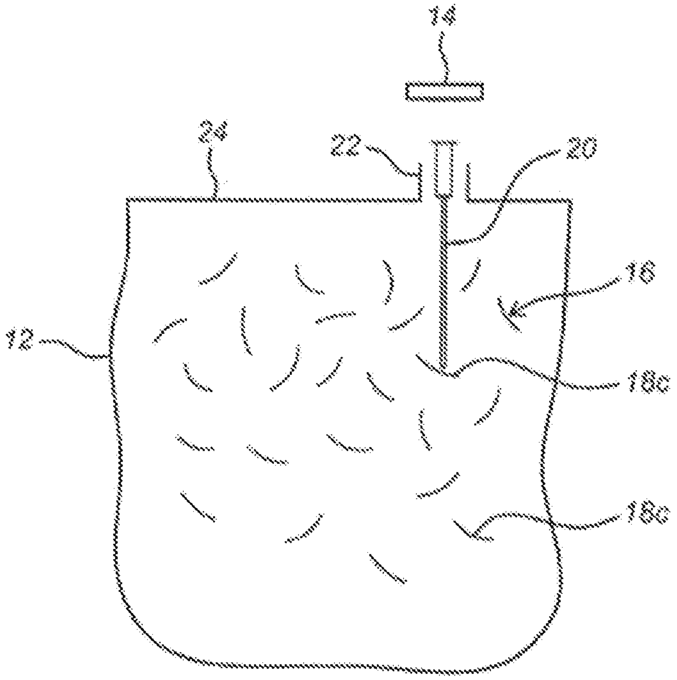
FIG. 1B is a schematic view illustrating a sampler in use in an unstructured bed, where a positioner includes at least one fiber.
Figure 1C:
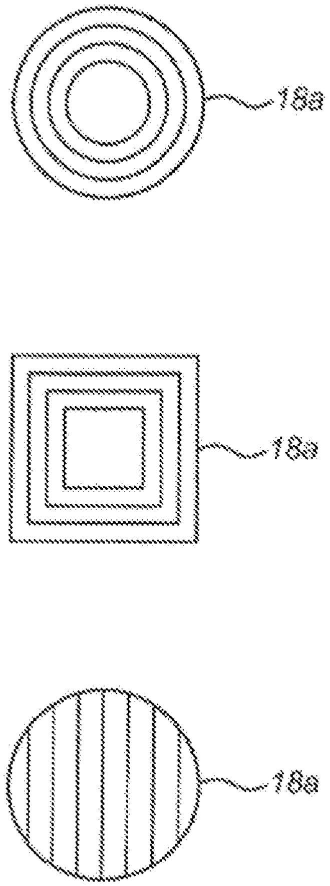
FIG. 1C illustrates alternate forms of a structured fixed bed.

While FIG. 1A illustrates a rolled, generally cylindrical arrangement for a structured fixed bed 18 (including cell immobilization and spacer layers 18*a*, 18*b*, which combination is optional), it should be appreciated that other forms may be used (including, for example, just one cell immobilization layer or multiple spacer layers, either of which may be folded like an accordion). Thus, with reference to FIG. 1C, the fixed bed 18 may comprise a plurality of concentric layers 18*a* formed of a continuous material, and may be in any shape (e.g., circular, square, etc.). Alternatively, instead of being non-linear, the layers 18*a* may instead be linear. In any of these cases, spacer layers 18*b* may or may not be provided, and the sample portion 16 may be located at any location (or locations) within the bed 18, without limitation, depending on the particular application and/or the desired approach to sampling.

Returning to FIG. 1, an anchorage point may be adapted to form a seal with the cover or cap 14. This anchorage point may comprise, for instance, a sidewall of the port 22 associated with the lid 24 of the bioreactor 12. The cap 14 associated with the sampler 10 may be releasably connected to the port 22. This may be achieved by threading or other means of secure, but releasable connection (e.g., a bayonet fitting, as further outlined in the following description, or a door with a releasable latch (push-pull type of arrangement, or even a friction or interference fit)).

To ensure that cell growth is achieved on the sample portion 16 in the illustrated format, the positioner 20 may extend a distance sufficient to ensure that the sample portion 16 is at least partially positioned within or adjacent to the fixed bed 18, such as between two adjacent layers (e.g., between cell immobilization layers 18*a* arranged in direct contact, or separated by a spacer layer 18*b*). As can be appreciated, this distance may vary depending on the size and shape of the bioreactor 12, as well as the desired location for the sampling to occur, the type of bed, or the type of culture.

The positioner 20 may be connected to the cover or cap 14 serving as the support, but may also be separate therefrom (such that the cap 14 may be removed while the positioner 20 remains in position, which positioner 20 can then be withdrawn and the cap 14 replaced). The former version may be applied more readily to a non-structured fixed bed, such as shown in FIG. 1B, which allows the positioner 20 to be passed through the port 22 for positioning in the non-structured material within the non-structured fixed bed. A structured fixed bed is better suited for the latter version, since the sample portion 16 may be pre-positioned within or adjacent to the structured fixed bed layers and held in place thereby, and the positioner 20 later associated with the cap 14 (if desired).

In any disclosed embodiment, the spacer layers and/or the cell immobilization layers which make up respectively the spacer section (when present) and the immobilization section in the matrix assembly may comprise a biocompatible polymer. As examples the biocompatible polymer may be selected from polyester, polyethylene, polypropylene, polyamide, plasma treated polyethylene, plasma treated polyester, plasma treated polypropylene or plasma treated polyamide. The layers can be hydrophilic or hydrophobic, with a preference for the former in terms of the cell immobilization layers.

The thickness of the one or more layers may vary depending on the application, and may be between 0.05 mm and 3 mm, between 0.1 and 2 mm, or between 0.1 and 1 mm. Suitable material for the cell immobilization layer may be a woven or nonwoven material. A nonwoven, contrary to a woven material, is a fabric which is not created by weaving or knitting and does not require converting the fibers to yarn. Nonwovens are broadly defined as sheet or web structures bonded together by entangling fiber or filaments (and by perforating films) mechanically, thermally or chemically. The nature of the nonwoven material used in the current application may be of any origin, either comprising of natural fibers or synthetic fibers. By preference, the nonwoven is made of a polymer, such as polyester or polypropylene. The cell immobilization layers may comprise a polyethylete terepthalate (PET) nonwoven. The nonwoven material may be plasma treated to enhance cell adherence and flow.

The one or more layers may comprise a substrate including a plurality of openings configured to allow flow of at least one of cell culture media, cells, or cell products through the thickness of the substrate. The substrate can be at least one of a molded polymer lattice sheet, a 3D-printed lattice sheet, and a woven mesh sheet. The substrate may have a regular, ordered structure and provide a surface for cell adhesion, growth, and eventual cell release. The substrate may comprise a mesh fabricated from monofilament or multifilament fibers of polymeric materials compatible in cell culture applications, including, for example, polystyrene, polyethylene terephthalate, polycarbonate, polyvinylpyrrolidone, polybutadiene, polyvinylchloride, polyethylene oxide, polypyrroles, and polypropylene oxide. Mesh substrates may have a different patterns or weaves, including, for example knitted, warp-knitted, or woven (e.g., plain weave, twilled weave, dutch weave, five needle weave). A non-woven mesh may have a fiber diameter of about 20 μm, a thickness of about 0.18 mm, and a porosity of 91%. A woven mesh substrate may have a diameter of about 160 μm and an opening diameter of 250 μm.

The spacer layers may comprise a (biocompatible) polymer with mesh size as described above. In one embodiment, the spacer layer is a synthetic woven fabric or structure. In another embodiment, the spacer layer is a bearing structure. Such structure may be produced from a biopolymer (e.g. alginate). Other suitable material for this purpose is silica, polystyrene, agarose, styrene divinylbenzene, polyacrylonitrile or latex. The spacer layer may be gamma irradiated in order to reduce bioburden.

The design of the matrix assembly may take many forms depending on the application and type of bioreactor. In one embodiment, the immobilization section and spacer section are alternately positioned. "Alternately positioned" means that each spacer section is followed by a cell immobilization section which is itself followed by a spacer section. These alternately positioned sections may alternate in vertical position or in a horizontal position according to the use of the matrix and/or to the bioreactor in which the matrix is introduced. In this embodiment, one or more layers of cell immobilization layers are superimposed on one or more spacer layers (or vice versa). This configuration may be repeated several times if deemed desirable in order creating a stack of several immobilization and spacer sections. Ideally, the end configuration may comprise between 1 and 500 alternations of the above described layering. The stacked layers may be positioned in a frame or cassette or sealed/connected at their circumference. In another embodiment, the achieved stack can be rolled around an axis or core to achieve a spiral configuration.

The substrate used for either the immobilization section and spacer section can be chosen based on the application, characteristics of the layers (dimensions, size, etc.) and desired result. Hence, the number of layers within either immobilization section or spacer section may be between 1 and 20, between 1 and 10, or between 1 and 5.

The optional spacer section(s), if present, create space inside the matrix assembly through which the culture medium flows. This provides improved circulation of the culture medium through the matrix assembly, thereby ensuring it reaches all cultured cells. This effect is even more enhanced in the embodiment wherein the spacer section comprises one spacer layer and the cell immobilization section comprises two immobilization layers. The culture medium flowing inside the matrix assembly via the spacer sections is tangentially oriented with respect to the cell immobilization sections.

According to one aspect of the disclosure, and with reference to FIG. 2, a sampler 100 for sampling a cell culture may be provided. The sampler 100 may include a positioner 120 having a removable portion 102 depending therefrom, with a sample portion 116 at a distal end portion thereof. This removable portion 102 may comprise an elongated pair of spaced apart members 102*a*, 102*b* connected at one end to a body 104. This arrangement allows the members 102*a*, 102*b* to move or flex inwardly toward each other as shown in FIG. 3, but could also be a one-piece structure and adapted for coupling to and decoupling from the sample portion 116.

At the other, proximal end, the members 102*a*, 102*b* may be adapted to connect with a part by which the sampler 100 may be grasped, such as a grip 106. Such grip can include any handle or similar mode of grasping by an operator. Specifically, each member 102*a*, 102*b* may include head portions 102*c*, 102*d* forming barbs or catches. When inserted into a passage 108 in the grip 106, the head portions 102*c*, 102*d* engage a ledge 106*a* in a normal or home position (see also FIG. 12). Simultaneously depressing or squeezing the members 102*a*, 102*b* toward one another, as indicated by opposed action arrows A in FIG. 3, allows the head portions 102*c*, 102*d* to move radially inwardly for passing outwardly in an axial direction through the passage 108, thereby releasing the removable portion 102 from the grip 106.

Initial or reinsertion of the removable portion 102 to connect with the grip 106 proceeds in a similar manner, with initial depression of the members 102*a*, 102*b*, but with insertion inwardly in the axial direction and then release to form the connection. As can be appreciated, this allows for reuse of the sampler 100 by adding a replacement removable portion 102 once used. This also potentially allows for retrofitting in connection with the grip 106 (which as outlined herein may also form part of a cap for sealing a port on the bioreactor).

Figure 5:
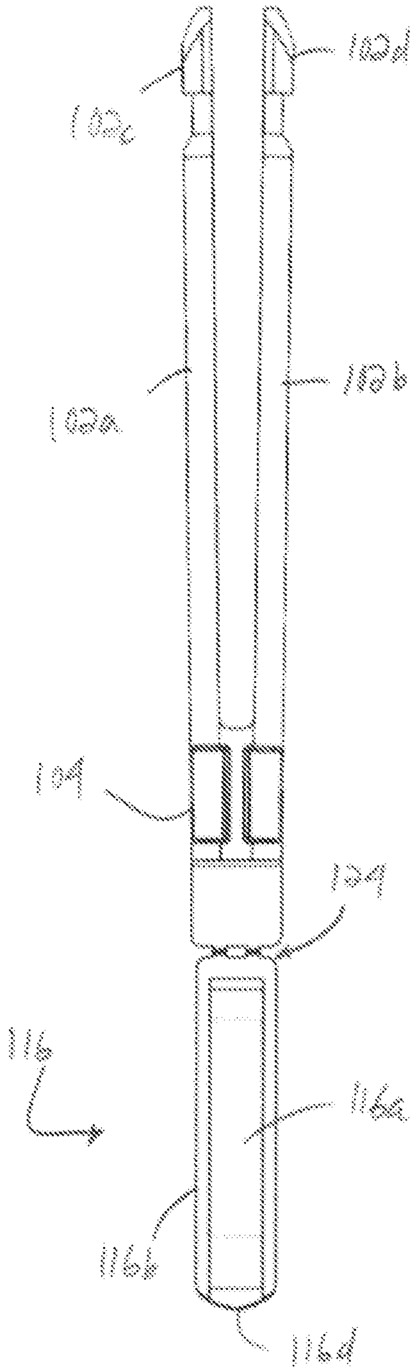
Figure 6:
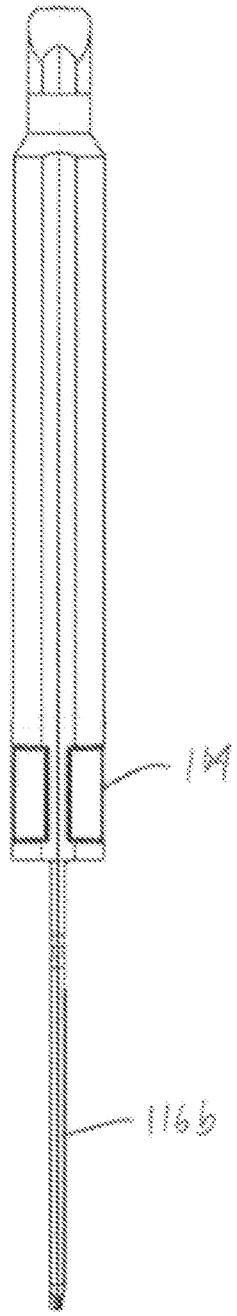
Figure 5A:
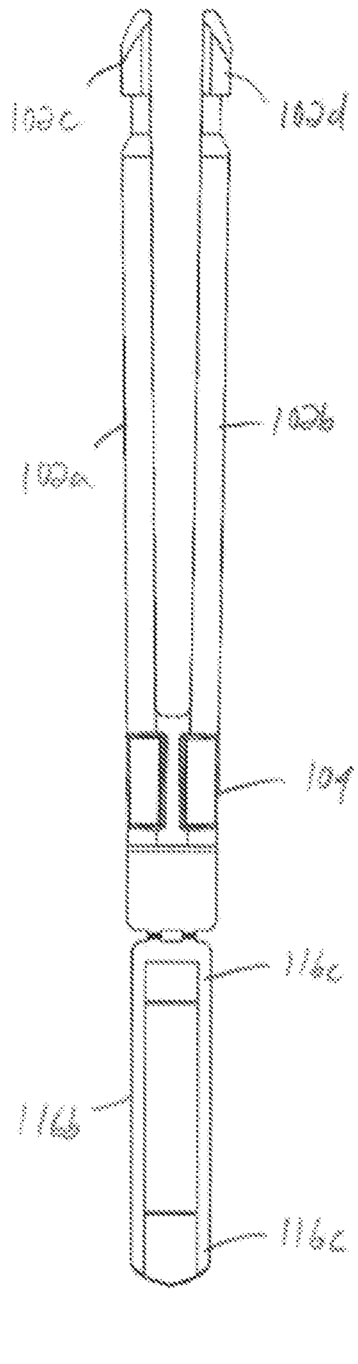
Figure 5B:
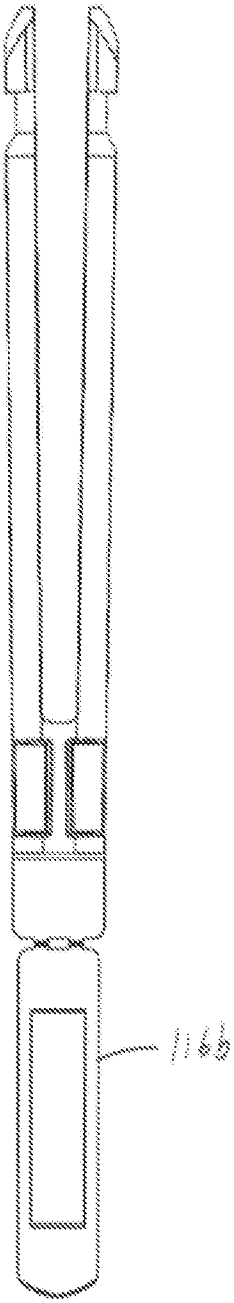

As perhaps best understood from FIGS. 5, 5A, and 5B, the sample portion 116 includes a substrate 116*a* for growing cells, which may be as previously described. The substrate 116*a* may be positioned within an opening O or window in a frame 116*b* of the sample portion 116, and may be recessed within it (see FIGS. 5A, 5B, showing recessed substrate mounting portions 116*c* associated with the frame 116*b*, and FIG. 6, noting thin profile of frame 116*b* when including the recessed). This may promote fluid flow around or along the substrate 116*a* when positioned within a cell culture bed, such as between layers of a fixed bed. A tip 116*d* of the sample portion 116 may be chamfered, pointed or sharpened to facilitate insertion between adjacent layers of the fixed bed with minimal or no disruption. The frame 116*b* may also be sufficiently rigid to facilitate insertion into the cell culture bed, such as between layers of it, without bending or folding, thereby ensuring that the substrate 116*a* remains present in the optimum position for cell attachment and growth once positioned in the bed.

In order to undergo further processing, the sample portion 116 may be releasably attached to the sampler 100. In one example, this releasability is achieved by providing a frangible connection 124 between one end of the sample portion 116 and the body 104 of the removable portion 102. This frangible connection 124 may be achieved by providing two connecting portions of material that can be easily broken away to separate the sample portion 116 from the body 104. This allows for the simple and rapid detachment, and thus, release, of the sample portion 116 once removed from the cell culture, such as in a manner outlined further in the following description. As noted above, replacement of the removable portion 102 with a new sample portion 116 then allows for the sampling to be repeated anew, if desired.

In order to recover cells from the sample portion 116 to understand the cell density or other aspects of the culture, a container 200, such as an EPPENDORF tube, may be provided for receiving the sample portion 116, possibly along with a solution for promoting detachment of cells from the substrate 116*a*. A removable insert 202 may be adapted for positioning within the container 200. This insert 202 may comprise a passage, such as a slot 203, for receiving the sample portion 116. The insert 202 may be sized and shaped to occupy a substantial volume of the interior compartment of the container 200 (together with the sample portion 116 when present; see FIG. 10), thereby reducing the amount of cell detachment solution required to be present without hampering cell detachment.

The insert 202 may also be adapted to assist in releasing the sample portion 116 from the sampler 100. For example, as shown in FIGS. 7 and 8, upper end portions 202*b* of the insert 202 may be chamfered, such that a ledge 202*c* is created. Thus, when the sample portion 116 still connected to the sampler 100 is inserted into the insert 202, as shown in FIG. 9, the removable portion 102 of the sample portion 116 may be moved in a direction toward and/or away from the ledges 202*a* (note arrow B in FIG. 9A), possibly in a repeated fashion. The resulting bending of the material assists in breaking the two apart, such as along the frangible connection 124, and thereby releases the sample portion (116' in FIG. 10) into the container 200. The container 200 including the insert 202, sample portion 116, and any detachment solution may then undergo further processing, such as collecting the removed cells using centrifugation. Instead of a frangible connection 124, any form of releasable attachment may serve to provide the releasability of the sample portion 116 from the sampler 100.

FIG. 11 shows a bioreactor 12 with a fixed bed 18 including a sample portion 16 connected to a positioner 20. The positioner 20 may be connected to or accessible via a cap 14 covering a port on the bioreactor lid 24. This figure illustrates in particular one exemplary flow pattern through the bioreactor, which may be caused by an internal agitator, such as an impeller I. The flow arrangement may be such that fluid passes downwardly (arrow D) through an inner chamber, and then in a forward run (arrow F) to pass upwardly (arrow U) through the fixed bed 18 located outboard of the inner chamber. Flow is then returned (arrow R) via an internal column, where it may be exposed to a gas (air). As can be appreciated, with the same structural arrangement, the flow could be reversed.

As can be appreciated from the cross-sectional view of FIGS. 12, 12A, and 12B, the sampler 100 may be integrally formed with one or more of the caps 14 for closing the ports of the bioreactor 12. For example, the cap 14 may comprise the grip 106 for receiving the removable positioner 120 connected to the sample portion 116 positioning within the cell culture, such as between layers of a fixed bed 118 (illustrated as a spiral configuration). The cap 14 may further include a seal 140 for sealing the associated port when positioned therein to assist in maintaining aseptic conditions.

With further reference to FIGS. 13 and 14, the sampler 100 including the grip 106 may have a locked position in which it is secured within a port 122 (FIG. 13), and an unlocked position where it may be withdrawn from the port (FIG. 14), which may be associated with a lid or cover of the bioreactor. As can be seen in FIGS. 12B and 14, the portion of the sampler 100 within the port 122 may include a connector, such as a radially outwardly directed projection 148 adapted to engage a mating connector, such as a radially inwardly directed projection 150 within the port 122 when the sampler 100 is rotated to a certain position, thereby preventing withdrawal. Rotation of the sampler 100 within the port 122 then releases the engagement between the projections 148, 150 from engagement and allows for the withdrawal of the sampler 100. Since the removable portion 102 is not directly attached to the grip 106, interference with the position of the sample portion 116 in the bed is not impacted by this rotation.

Likewise, during installation, the sampler 100 may be inserted into the port 122 with the projections 148, 150 out of alignment. The sampler 100 may then be rotated to form the locking engagement, again without disturbing the bed. The locked and unlocked positions may be indicated by indicia, such as on the grip 106, to facilitate the correct positioning for achieving the desired positioning.

While the bioreactor 12 is shown in a vertical orientation, it could be used in any orientation including for any layers present. For example, in FIG. 15, the bulk flow direction of the bioreactor 302 is in a direction from the inlet 310 to the outlet 312, and, in this example, the first and second major sides of the layers 308 are perpendicular to the bulk flow direction. The sampler 100 may in such case may be passed through a lid or cover 24 through openings in the layers 308.

In contrast, the example shown in FIG. 16 is of an embodiment in which the bioreactor 322 and stack of layers 328 within the culture space 324 have first and second sides that are parallel to a bulk flow direction, which corresponds to a direction shown by the flow lines into the inlets 330 and out of the outlets 332. The sampler 100 may pass through a port 22 in a sidewall of the bioreactor 322 to position the sample portion 116 between adjacent layers, but could also pass through the lid as noted.

A method of obtaining a sample of a cell culture in a fixed bed bioreactor may include using a sampler at least partially positioned in or adjacent to the fixed bed to promote the growth of cells on a releasably attached portion of the sampler. The method may involve initiating the cell culture process in the bioreactor, and allowing the process to run for a period of time to permit cell growth in the fixed bed and the releasably attached portion. The sampler may then be withdrawn from the bioreactor, and the releasably attached portion detached from the sampler (which may involve inserting the releasably attached portion into an opening of an insert in a container, and using the insert to break the portion from the sampler).

As used herein, the following terms have the following meanings:

"A", "an", and "the" as used herein refers to both singular and plural referents unless the context clearly dictates otherwise. By way of example, "a compartment" refers to one or more than one compartment.

"About," "substantially," or "approximately," as used herein referring to a measurable value, such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows and do not exclude or preclude the presence of additional, non-recited components, features, element, members, steps, known in the art or disclosed therein.

While certain preferred embodiments have been shown and described herein, it will be obvious to those skilled in the art that such embodiments are provided by way of example only. Numerous variations, changes, and substitutions will now occur to those skilled in the art without departing from the invention. For example, other forms of frangible connections may also be used, such as for example a perforated tear line, zipper, latch and hinge (living or otherwise), or other similar arrangements. It should be understood that various alternatives to the embodiments of the invention described herein may be employed in practicing the invention. It is intended that the following claims define the scope of the protection under the applicable law and that methods and structures within the scope of these claims and their equivalents be covered thereby.

What is claimed:

1. A bioreactor with integrated cell sampling capability, comprising:

a housing including a sampling port;

a fixed bed positioned within the housing; and a cell sampler extending through the sampling port, the cell sampler being releasably attached to a sample portion positioned within or adjacent to the fixed bed, wherein the sample portion comprises a frame including a window, with a substrate positioned within the window, said substrate adapted for growing cells thereon during cell culture;

wherein the frame of the sample portion is connected to the cell sampler by a frangible connection comprising at least one integrally formed breakaway connecting portion configured to fracture upon bending to detach the sample portion from the cell sampler; and wherein the frame extends from the frangible connection at a top of the frame above the substrate to a position below the substrate at a bottom of the frame.

2. The apparatus of claim 1, wherein the sampler includes a positioner adapted for positioning the releasably attached sample portion within or adjacent to the fixed bed.

3. The apparatus of claim 2, wherein the positioner is associated with the sampling port.

4. The apparatus of claim 3, wherein the bioreactor includes a cap for sealing the sampling port.

5. The apparatus of claim 1, wherein the sampler is releasable from a grip located external to the bioreactor.

6. The apparatus of claim 1, wherein the sampler is adapted for selectively forming a locking engagement with the bioreactor housing.

7. The apparatus of claim 1, wherein the bioreactor housing includes a lid and the lid comprises the sampling port.

8. The apparatus of claim 6, wherein the fixed bed comprises a plurality of layers, the releasably attached sample portion of the sampler being positioned between the plurality of layers.

9. An apparatus for sampling a cell culture associated with a fixed bed in a bioreactor having a port, comprising:

a sampler including a grip releasably connected to a positioner, the positioner connected to a sample portion adapted for positioning in the bioreactor adjacent the fixed bed, the sample portion including a frame including a window, said frame being releasably connected to the positioner, the frame receiving a substrate within the window, said substrate adapted for growing cells;

wherein the frame extends from the positioner at a top of the frame above the substrate to a position below the substrate at a bottom of the frame.

10. The apparatus of claim 9, wherein the sampler is adapted for selectively forming a locking engagement with the bioreactor.

11. The apparatus of claim 9, wherein the frame is releasably attached to the positioner by a frangible connection.

12. A kit for sampling a fixed bed of a bioreactor, comprising:

a sampler for sampling the fixed bed, the sampler including a cap adapted to engage a portion of the bioreactor, a positioner extending from the cap into the bioreactor, and a sample portion comprising a frame supporting a substrate adapted for growing cells, said frame extending from the positioner at a top of the frame above the substrate to a position below the substrate at a bottom of the frame;

means for releasably attaching the sample portion from the positioner; and a container adapted to detach the sample portion from the sampler.

13. The kit of claim 12, wherein the container includes an insert for receiving the sample portion, the insert adapted to facilitate detaching the sample portion from the sampler.

14. A method of obtaining a sample of a cell culture in a fixed bed bioreactor including a sampler at least partially positioned in or adjacent to the fixed bed to promote the growth of cells on a releasably attached portion of the sampler, comprising:

providing a cell sampler extending into the bioreactor, the cell sampler being releasably attached to a sample portion positioned within or adjacent to the fixed bed, wherein the sample portion is connected to the cell sampler by a frangible connection comprising two integrally formed, breakaway connecting portions configured to fracture upon bending to detach the sample portion from the sampler, and wherein the sample portion comprises a frame housing a substrate adapted for growing cells, the frame extending from the frangible connection at a top of the frame above the substrate to a bottom of the frame below the substrate;

initiating the cell culture process in the bioreactor;

allowing the process to run for a period of time to permit cell growth in the fixed bed and the releasably attached portion;

withdrawing the sampler from the bioreactor; and detaching the releasably attached portion from the sampler.

15. The method of claim 14, wherein the detaching step comprises inserting the releasably attached portion into an opening of an insert in a container, and using the insert to break the portion from the sampler.

* * * * *